US010416173B2

(12) United States Patent
Dammeier et al.

(10) Patent No.: US 10,416,173 B2
(45) Date of Patent: Sep. 17, 2019

(54) METHOD FOR THE DIAGNOSIS OF OR RISK FOR A DISEASE MEDIATED VIA THE ALTERNATIVE PATHWAY OF THE COMPLEMENT SYSTEM (71) Applicant: Eberhard Karls Universitaet Tuebingen Medizinische Fakultaet, Tuebingen (DE)

(72) Inventors: Sascha Dammeier, Tuebingen (DE); Eloed Koertvély, Dettenhausen (DE); Marius Ueffing, Tuebingen (DE)

(73) Assignee: Eberhard Karls Universitaet Tuebingen Medizinische Fakultaet, Tuebingen (DE)

( * ) Notice: Subject to any disclaimer, the term of this patent is extended or adjusted under 35 U.S.C. 154(b) by 0 days.

(21) Appl. No.: 15/362,304

(22) Filed: Nov. 28, 2016

(65) Prior Publication Data
US 2017/0160291 A1 Jun. 8, 2017

Related U.S. Application Data (63) Continuation of application No. PCT/EP2015/061437, filed on May 22, 2015.

(30) Foreign Application Priority Data

May 26, 2014 (DE) .................. 10 2014 107 380

(51) Int. Cl.
*G01N 33/68* (2006.01)
(52) U.S. Cl.
CPC ......... *G01N 33/6893* (2013.01); *G01N 33/68* (2013.01); *G01N 2333/4716* (2013.01)
(58) Field of Classification Search
None
See application file for complete search history.

(56) References Cited

U.S. PATENT DOCUMENTS

| | | | |
|---|---|---|---|
| 2003/0092620 | A1 | 5/2003 | Lucas et al. |
| 2013/0040851 | A1 | 2/2013 | Hanzawa et al. |
| 2013/0149389 | A1 | 6/2013 | Flora et al. |

FOREIGN PATENT DOCUMENTS

| | | |
|---|---|---|
| EP | 0 287 509 A1 | 10/1988 |
| RU | 2232991 C1 | 7/2004 |
| WO | WO 2007/030919 A1 | 3/2007 |
| WO | WO 2007/141004 A1 | 12/2007 |
| WO | WO 2008/106644 A2 | 9/2008 |
| WO | WO 2008/137236 A2 | 11/2008 |
| WO | WO 2009/017405 A2 | 2/2009 |
| WO | WO 2010/075519 A2 | 7/2010 |
| WO | WO 2011/136080 A1 | 11/2011 |
| WO | WO 2012/146778 A2 | 11/2012 |
| WO | WO 2012/170556 A1 | 12/2012 |
| WO | WO 2013/071702 A1 | 5/2013 |
| WO | WO 2013/071703 A1 | 5/2013 |

OTHER PUBLICATIONS

Li et al in PNAS (77:3211-3214, 1980) (Year: 1980).*
Lederman et al in Molecular Immunology (28:1171-1181, 1991) (Year: 1991).*
Abaza et al in Journal of Protein Chemistry (11(5):433-444, 1992) (Year: 1992).*
Colman et al in Research in Immunology (145(1):33-36, 1994) (Year: 1994).*
Bienertová-Vašků 2011 "Adipsin (Complement Factor D) As a New Biomarker of Body Fat Distribution in Extremely Obese Central-European Populations" in *Body Fat: Composition, Measurements and Reduction Procedures* Nova Science Publishers, Inc., Julie Bienertova-Vasku Editor, pp. 149-161.
Bjellqvist, B. et al. 1993 "The focusing positions of polypeptides in immobilized pH gradients can be predicted from their amino acid sequences" *Electrophoresis* 14: 1023-1031.
Hollers, V.M. 2008 "The spectrum of complement alternative pathway-mediated diseases" *Immunological Reviews* 223: 300-316.
International Preliminary Report on Patentability (English Translation), issued in PCT/EP2015/061437, dated Nov. 28, 2016.
International Search Report in PCT/EP2015/061437, dated Jul. 7, 2015.
Lo, J.C. et al. 2014 "Adipsin Is an Adipokine that Improves β Cell Function in Diabetes" *Cell* 158: 41-53.
Min, H.Y. and Spiegelman, B.M. 1986 "Adipsin, the adipocyte serine protease: gene structure and control of expression by tumor necrosis factor" *Nucleic Acids Research* 14: 8879-8892.
Miner, J.L. et al. 1993 "Adipsin expression and growth in rats as influenced by insulin and somatotropin" *Physiology & Behavior* 54: 207-212.
Prentice, R.L. et al. 2013 "Proteomic risk markers for coronary heart disease and stroke: validation and mediation of randomized trial hormone therapy effects on these diseases" Genome Medicine 5:112 (in 15 pages).
Searfoss, G.H. et al. 2003 "Adipsin, a Biomarker of Gastrointestinal Toxicity Mediated by a Functional γ-Secretase Inhibitor" *J Biol Chem* 278: 46107-46116.
Sprong, T. et al. 2006 "Deficient alternative complement pathway activation due to factor D deficiency by 2 novel mutations in the complement factor D gene in a family with meningococcal infections" *Blood* 207: 4865-4970.
Uniprotkb/Swiss-Prot Accession No. P03953.1, created and available Oct. 23, 1986.

(Continued)

*Primary Examiner* — Changhwa J Cheu
(74) *Attorney, Agent, or Firm* — Knobbe, Martens, Olson & Bear LLP (57) ABSTRACT The present invention relates to a method for the diagnosis of a disease or a risk for the development of a disease, in particular a disease which is mediated via the alternative pathway of the complement system. It further relates to a novel diagnostic marker and methods for identifying active agents.

7 Claims, 4 Drawing Sheets
Specification includes a Sequence Listing.

(56) References Cited

OTHER PUBLICATIONS

Yamauchi, Y. et al. 1994 "Recombinant and Native Zymogen Forms of Human Complement Factor D" *J Immunol* 152: 3645-3653.
Biesma, D.H. et al. 2001 "A family with complement factor D deficiency" *J Clin Invest* 108: 233-240.
Wikipedia definition for "Protein isoform" from the internet at: en.wikipedia.org/wiki/Protein_isoform, downloaded Nov. 21, 2007.

* cited by examiner

```
SEQUENCE LISTING

<160> NUMBER OF SEQ ID NOS: 13

<210> SEQ ID NO 1
<211> LENGTH: 228
<212> TYPE: PRT
<213> ORGANISM: Homo sapiens

<400> SEQUENCE: 1

Ile Leu Gly Gly Arg Glu Ala Glu Ala His Ala Arg Pro Tyr Met Ala
1               5                   10                  15

Ser Val Gln Leu Asn Gly Ala His Leu Cys Gly Gly Val Leu Val Ala
            20                  25                  30

Glu Gln Trp Val Leu Ser Ala Ala His Cys Leu Glu Asp Ala Ala Asp
        35                  40                  45

Gly Lys Val Gln Val Leu Leu Gly Ala His Ser Leu Ser Gln Pro Glu
    50                  55                  60

Pro Ser Lys Arg Leu Tyr Asp Val Leu Arg Ala Val Pro His Pro Asp
65                  70                  75                  80

Ser Gln Pro Asp Thr Ile Asp His Asp Leu Leu Leu Leu Gln Leu Ser
                85                  90                  95

Glu Lys Ala Thr Leu Gly Pro Ala Val Arg Pro Leu Pro Trp Gln Arg
            100                 105                 110

Val Asp Arg Asp Val Ala Pro Gly Thr Leu Cys Asp Val Ala Gly Trp
        115                 120                 125

Gly Ile Val Asn His Ala Gly Arg Arg Pro Asp Ser Leu Gln His Val
    130                 135                 140

Leu Leu Pro Val Leu Asp Arg Ala Thr Cys Asn Arg Arg Thr His His
145                 150                 155                 160

Asp Gly Ala Ile Thr Glu Arg Leu Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
        195                 200                 205

Lys Pro Gly Ile Tyr Thr Arg Val Ala Ser Tyr Ala Ala Trp Ile Asp
    210                 215                 220

Ser Val Leu Ala
225

<210> SEQ ID NO 2
<211> LENGTH: 233
<212> TYPE: PRT
<213> ORGANISM: Homo sapiens

<400> SEQUENCE: 2
```

```
Pro Pro Arg Gly Arg Ile Leu Gly Gly Arg Glu Ala Glu Ala His Ala
1               5                   10                  15

Arg Pro Tyr Met Ala Ser Val Gln Leu Asn Gly Ala His Leu Cys Gly
                20                  25                  30

Gly Val Leu Val Ala Glu Gln Trp Val Leu Ser Ala Ala His Cys Leu
            35                  40                  45

Glu Asp Ala Ala Asp Gly Lys Val Gln Val Leu Leu Gly Ala His Ser
    50                  55                  60

Leu Ser Gln Pro Glu Pro Ser Lys Arg Leu Tyr Asp Val Leu Arg Ala
65                  70                  75                  80

Val Pro His Pro Asp Ser Gln Pro Asp Thr Ile Asp His Asp Leu Leu
                85                  90                  95

Leu Leu Gln Leu Ser Glu Lys Ala Thr Leu Gly Pro Ala Val Arg Pro
                100                 105                 110

Leu Pro Trp Gln Arg Val Asp Arg Asp Val Ala Pro Gly Thr Leu Cys
            115                 120                 125

Asp Val Ala Gly Trp Gly Ile Val Asn His Ala Gly Arg Arg Pro Asp
    130                 135                 140

Ser Leu Gln His Val Leu Leu Pro Val Leu Asp Arg Ala Thr Cys Asn
145                 150                 155                 160

Arg Arg Thr His His Asp Gly Ala Ile Thr Glu Arg Leu Met Cys Ala
                165                 170                 175

Glu Ser Asn Arg Arg Asp Ser Cys Lys Gly Asp Ser Gly Gly Pro Leu
                180                 185                 190

Val Cys Gly Gly Val Leu Glu Gly Val Val Thr Ser Gly Ser Arg Val
            195                 200                 205

Cys Gly Asn Arg Lys Lys Pro Gly Ile Tyr Thr Arg Val Ala Ser Tyr
    210                 215                 220

Ala Ala Trp Ile Asp Ser Val Leu Ala
225                 230

<210> SEQ ID NO 3
<211> LENGTH: 232
<212> TYPE: PRT
<213> ORGANISM: Homo sapiens

<400> SEQUENCE: 3

Pro Arg Gly Arg Ile Leu Gly Gly Arg Glu Ala Glu Ala His Ala Arg
1               5                   10                  15

Pro Tyr Met Ala Ser Val Gln Leu Asn Gly Ala His Leu Cys Gly Gly
                20                  25                  30

Val Leu Val Ala Glu Gln Trp Val Leu Ser Ala Ala His Cys Leu Glu
            35                  40                  45

Asp Ala Ala Asp Gly Lys Val Gln Val Leu Leu Gly Ala His Ser Leu
    50                  55                  60

Ser Gln Pro Glu Pro Ser Lys Arg Leu Tyr Asp Val Leu Arg Ala Val
65                  70                  75                  80

Pro His Pro Asp Ser Gln Pro Asp Thr Ile Asp His Asp Leu Leu Leu
                85                  90                  95

Leu Gln Leu Ser Glu Lys Ala Thr Leu Gly Pro Ala Val Arg Pro Leu
                100                 105                 110

Pro Trp Gln Arg Val Asp Arg Asp Val Ala Pro Gly Thr Leu Cys Asp
            115                 120                 125

Val Ala Gly Trp Gly Ile Val Asn His Ala Gly Arg Arg Pro Asp Ser
```

```
                130             135             140
Leu Gln His Val Leu Leu Pro Val Leu Asp Arg Ala Thr Cys Asn Arg
145                 150                 155                 160

Arg Thr His His Asp Gly Ala Ile Thr Glu Arg Leu Met Cys Ala Glu
                165                 170                 175

Ser Asn Arg Arg Asp Ser Cys Lys Gly Asp Ser Gly Pro Leu Val
                180                 185                 190

Cys Gly Gly Val Leu Glu Gly Val Val Thr Ser Gly Ser Arg Val Cys
            195                 200                 205

Gly Asn Arg Lys Lys Pro Gly Ile Tyr Thr Arg Val Ala Ser Tyr Ala
            210                 215                 220

Ala Trp Ile Asp Ser Val Leu Ala
225                 230

<210> SEQ ID NO 4
<211> LENGTH: 231
<212> TYPE: PRT
<213> ORGANISM: Homo sapiens

<400> SEQUENCE: 4

Arg Gly Arg Ile Leu Gly Gly Arg Glu Ala Glu Ala His Ala Arg Pro
1               5                   10                  15

Tyr Met Ala Ser Val Gln Leu Asn Gly Ala His Leu Cys Gly Gly Val
                20                  25                  30

Leu Val Ala Glu Gln Trp Val Leu Ser Ala Ala His Cys Leu Glu Asp
            35                  40                  45

Ala Ala Asp Gly Lys Val Gln Val Leu Leu Gly Ala His Ser Leu Ser
        50                  55                  60

Gln Pro Glu Pro Ser Lys Arg Leu Tyr Asp Val Leu Arg Ala Val Pro
65                  70                  75                  80

His Pro Asp Ser Gln Pro Asp Thr Ile Asp His Asp Leu Leu Leu Leu
                85                  90                  95

Gln Leu Ser Glu Lys Ala Thr Leu Gly Pro Ala Val Arg Pro Leu Pro
                100                 105                 110

Trp Gln Arg Val Asp Arg Asp Val Ala Pro Gly Thr Leu Cys Asp Val
            115                 120                 125

Ala Gly Trp Gly Ile Val Asn His Ala Gly Arg Arg Pro Asp Ser Leu
        130                 135                 140

Gln His Val Leu Leu Pro Val Leu Asp Arg Ala Thr Cys Asn Arg Arg
145                 150                 155                 160

Thr His His Asp Gly Ala Ile Thr Glu Arg Leu Met Cys Ala Glu Ser
                165                 170                 175

Asn Arg Arg Asp Ser Cys Lys Gly Asp Ser Gly Gly Pro Leu Val Cys
            180                 185                 190

Gly Gly Val Leu Glu Gly Val Val Thr Ser Gly Ser Arg Val Cys Gly
        195                 200                 205

Asn Arg Lys Lys Pro Gly Ile Tyr Thr Arg Val Ala Ser Tyr Ala Ala
    210                 215                 220

Trp Ile Asp Ser Val Leu Ala
225                 230

<210> SEQ ID NO 5
<211> LENGTH: 230
<212> TYPE: PRT
<213> ORGANISM: Homo sapiens
```

<400> SEQUENCE: 5

Gly Arg Ile Leu Gly Gly Arg Glu Ala Glu Ala His Ala Arg Pro Tyr
1               5                   10                  15

Met Ala Ser Val Gln Leu Asn Gly Ala His Leu Cys Gly Gly Val Leu
            20                  25                  30

Val Ala Glu Gln Trp Val Leu Ser Ala Ala His Cys Leu Glu Asp Ala
        35                  40                  45

Ala Asp Gly Lys Val Gln Val Leu Leu Gly Ala His Ser Leu Ser Gln
    50                  55                  60

Pro Glu Pro Ser Lys Arg Leu Tyr Asp Val Leu Arg Ala Val Pro His
65                  70                  75                  80

Pro Asp Ser Gln Pro Asp Thr Ile Asp His Asp Leu Leu Leu Leu Gln
                85                  90                  95

Leu Ser Glu Lys Ala Thr Leu Gly Pro Ala Val Arg Pro Leu Pro Trp
            100                 105                 110

Gln Arg Val Asp Arg Asp Val Ala Pro Gly Thr Leu Cys Asp Val Ala
        115                 120                 125

Gly Trp Gly Ile Val Asn His Ala Gly Arg Arg Pro Asp Ser Leu Gln
    130                 135                 140

His Val Leu Leu Pro Val Leu Asp Arg Ala Thr Cys Asn Arg Arg Thr
145                 150                 155                 160

His His Asp Gly Ala Ile Thr Glu Arg Leu Met Cys Ala Glu Ser Asn
                165                 170                 175

Arg Arg Asp Ser Cys Lys Gly Asp Ser Gly Gly Pro Leu Val Cys Gly
            180                 185                 190

Gly Val Leu Glu Gly Val Val Thr Ser Gly Ser Arg Val Cys Gly Asn
        195                 200                 205

Arg Lys Lys Pro Gly Ile Tyr Thr Arg Val Ala Ser Tyr Ala Ala Trp
    210                 215                 220

Ile Asp Ser Val Leu Ala
225                 230

<210> SEQ ID NO 6
<211> LENGTH: 229
<212> TYPE: PRT
<213> ORGANISM: Homo sapiens

<400> SEQUENCE: 6

Arg Ile Leu Gly Gly Arg Glu Ala Glu Ala His Ala Arg Pro Tyr Met
1               5                   10                  15

Ala Ser Val Gln Leu Asn Gly Ala His Leu Cys Gly Gly Val Leu Val
            20                  25                  30

Ala Glu Gln Trp Val Leu Ser Ala Ala His Cys Leu Glu Asp Ala Ala
        35                  40                  45

Asp Gly Lys Val Gln Val Leu Leu Gly Ala His Ser Leu Ser Gln Pro
    50                  55                  60

Glu Pro Ser Lys Arg Leu Tyr Asp Val Leu Arg Ala Val Pro His Pro
65                  70                  75                  80

Asp Ser Gln Pro Asp Thr Ile Asp His Asp Leu Leu Leu Leu Gln Leu
                85                  90                  95

Ser Glu Lys Ala Thr Leu Gly Pro Ala Val Arg Pro Leu Pro Trp Gln
            100                 105                 110

Arg Val Asp Arg Asp Val Ala Pro Gly Thr Leu Cys Asp Val Ala Gly
        115                 120                 125

```
Trp Gly Ile Val Asn His Ala Gly Arg Arg Pro Asp Ser Leu Gln His
            130                 135                 140

Val Leu Leu Pro Val Leu Asp Arg Ala Thr Cys Asn Arg Arg Thr His
145                 150                 155                 160

His Asp Gly Ala Ile Thr Glu Arg Leu Met Cys Ala Glu Ser Asn Arg
                165                 170                 175

Arg Asp Ser Cys Lys Gly Asp Ser Gly Pro Leu Val Cys Gly Gly
            180                 185                 190

Val Leu Glu Gly Val Val Thr Ser Gly Ser Arg Val Cys Gly Asn Arg
            195                 200                 205

Lys Lys Pro Gly Ile Tyr Thr Arg Val Ala Ser Tyr Ala Ala Trp Ile
    210                 215                 220

Asp Ser Val Leu Ala
225

<210> SEQ ID NO 7
<211> LENGTH: 10
<212> TYPE: PRT
<213> ORGANISM: Artificial Sequence
<220> FEATURE:
<223> OTHER INFORMATION: peptide

<400> SEQUENCE: 7

Pro Pro Arg Gly Arg Ile Leu Gly Gly Arg
1               5                   10

<210> SEQ ID NO 8
<211> LENGTH: 9
<212> TYPE: PRT
<213> ORGANISM: Artificial Sequence
<220> FEATURE:
<223> OTHER INFORMATION: peptide

<400> SEQUENCE: 8

Pro Arg Gly Arg Ile Leu Gly Gly Arg
1               5

<210> SEQ ID NO 9
<211> LENGTH: 8
<212> TYPE: PRT
<213> ORGANISM: Artificial Sequence
<220> FEATURE:
<223> OTHER INFORMATION: peptide

<400> SEQUENCE: 9

Arg Gly Arg Ile Leu Gly Gly Arg
1               5

<210> SEQ ID NO 10
<211> LENGTH: 7
<212> TYPE: PRT
<213> ORGANISM: Artificial Sequence
<220> FEATURE:
<223> OTHER INFORMATION: peptide

<400> SEQUENCE: 10

Gly Arg Ile Leu Gly Gly Arg
1               5

<210> SEQ ID NO 11
<211> LENGTH: 6
<212> TYPE: PRT
<213> ORGANISM: Artificial Sequence
<220> FEATURE:
```

```
<223> OTHER INFORMATION: peptide

<400> SEQUENCE: 11

Arg Ile Leu Gly Gly Arg
1               5

<210> SEQ ID NO 12
<211> LENGTH: 5
<212> TYPE: PRT
<213> ORGANISM: Artificial Sequence
<220> FEATURE:
<223> OTHER INFORMATION: peptide

<400> SEQUENCE: 12

Ile Leu Gly Gly Arg
1               5

<210> SEQ ID NO 13
<211> LENGTH: 30
<212> TYPE: PRT
<213> ORGANISM: Artificial Sequence
<220> FEATURE:
<223> OTHER INFORMATION: peptide

<400> SEQUENCE: 13

Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg
            20                  25                  30
```

METHOD FOR THE DIAGNOSIS OF OR RISK FOR A DISEASE MEDIATED VIA THE ALTERNATIVE PATHWAY OF THE COMPLEMENT SYSTEM

CROSS-REFERENCES TO RELATED APPLICATIONS

This application is a continuation of copending international patent application PCT/EP2015/061437 filed on 22 May 2015 and designating the U.S., which was not published under PCT Article 21(2) in English, and claims priority of German patent application DE 10 2014 107 380.0 filed on 26 May 2014, which is incorporated herein by reference.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 24705159_1.TXT, the date of creation of the ASCII text file is Nov. 28, 2016, and the size of the ASCII text file is 13.6 KB.

FIELD

The present invention relates to a method for the diagnosis of a disease or a risk for the development of a disease, in particular a disease which is mediated via the alternative pathway of the complement system. It further relates to a novel diagnostic marker and methods for identifying active agents.

BACKGROUND

The complement system is a system of plasma proteins which can be activated in the course of the immune response. It is part of the innate immune system. The human complement system consists of more than 30 proteins which are dissolved in the blood plasma or bound to cells. They have the function to protect against micro organisms, however they also have strong cell-destroying properties and may be, if unregulated, responsible for tissue damages in the course of many diseases.

A distinction is made between three pathways via which the complement system is activated, namely the classical pathway which is in most cases induced by antibodies, the lectin pathway which is activated by the mannose binding lectin, and the spontaneous and antibody independent alternative pathway.

A rate determining enzyme of the alternative pathway is the so-called complement factor D (CFD; EC 3.4.21.46) which is also referred to as adipsin or C3 proactivator convertase. CFD is a serine protease which is primarily synthesized in the fat tissue and secreted into the blood circulation. In addition, CFD can be found in different tissues. CFD cleaves the complement factor B. It is described that in the mammal cells the enzyme is synthesized as inactive proenzyme (proCFD) or zymogen and converted into the mature and active form, i.e. the CFD, by cleaving off 5 N terminal amino acids.

RELATED PRIOR ART

In the state of the art CFD is described as a biomarker in pathologically obese patients or animals: Bienertová-Vašků et al. (2011), Adipsin (Complement Factor D) as a new biomarker of body fat distribution in extremely obese central-European population, in "Body Fat: Composition, Measurements and Reduction Procedures", New York, Nova-publishers, p. 14-27; Searfoss et al. (2003), Adipsin, a biomarker of gastrointestinal toxicity mediated by a functional gamma-secretase inhibitor, J. Biol. Chem., Vol. 278 (46), p. 46107-46116; Miner et al. (1993), Adipsin expression and growth in rats as influenced by insulin and somatotropin, Physiol. Behav. Vol. 54(2), p. 207-212.

Furthermore, CFD is described as a risk marker with respect to a coronary heart disease: Prentice et al. (2013), Proteomic risk markers for coronary heart disease and stroke: validation and mediation of randomized trial hormone therapy effects on these diseases, Genome Med. Vol. 5(12):112.

CFD is associated with a variety of further diseases, as for example described in the following patent documents: WO 2012/170556, WO 2012/146778, WO 2011/136080, WO 2010/075519, WO 2008/137236, WO 2009/017405, RU 2232991, US 2003/092620, WO 2013/071702, WO 2013/071703, WO 2007/141004, WO 2007/030919, EP 0287509. The diseases associated with CFD can also be identified in the database "MalaCards" of the Weizmann Institute of Science (search entry "CFD").

In recent times such diseases which are mediated via the alternative pathway of the complement system have been in the center of interest. They are summarized in Holers (2008), The Spectrum of Complement Alternative Pathway-Mediated Diseases, Immunological Reviews, Vol. 223, pages 300 to 316.

Lo et al. (2014), Adipsin is an adipokine that improves better cell function in diabetes, Cell, 158(1): 41-53, describe a relationship between the alternative pathway of the complement system and the development of diabetes mellitus type 2. In a subgroup of examined patients a low level of CFD was determined, which correlated with an increased risk for a functional failure of the β cells. The authors express the wish for a method via which the patients can be classified with respect to their risk for a disease.

Spong et al. (2006), Deficient alternative complement pathway activation due to factor D deficiency by 2 novel mutations in the complement factor D gene in a family with meningococcal infections, Blood, 107: 4865-4870, describe point mutations in CFD which were identified in patients which are affected by a meningitis. By these point mutations the activation of the alternative pathway of the complement system would be impaired.

In the US 2003/0092620 methods for the treatment of different patients are described. It is mentioned that the patients in need can be identified by a genotyping of CFD with regard to single nucleotide polymorphisms (SNPs), or the mRNA level is determined on the basis of clinical samples.

The methods available in the prior art have not proved to be reliable in practice.

SUMMARY OF THE INVENTION

Against this background it is a problem underlying the invention to provide a method for the diagnosis of a disease or the risk for the development of a disease, in particular such a disease which is mediated via the alternative pathway of the complement system.

This problem is solved by a method for the diagnosis of a disease or a risk for the development of a disease in a living being, comprising the following steps:

(1) Provision of a biological sample of the living being,
(2) Examination of the biological sample for the presence of at least one isoform of the complement factor D (isoCFD),
(3) Making a positive diagnosis in case of a positive detection of at least one isoCFD in the biological sample, or making a negative diagnosis in case of a negative detection of at least one isoCFD in the biological sample.

The inventors have surprisingly realized that so far unknown isoforms of the complement factor D (CFD) can be found in a biological sample of a living being which became diseased or has a risk for the development of a disease, which isoforms cannot be found in a healthy reference living being or which are only below the detection limit.

This finding was surprising. There are suggestions in the state of the art to use CFD or proCFD as a biological or diagnostic marker, however not isoforms of CFD.

Isoforms of human CFD are largely unknown.

Yamauchi et al. (1994), Recombinant and native zymogen forms of human complement factor D, Journal of Immunology, Vol. 152, pages 3645 to 3653, describe an isoenzyme of CFD which was found in the urine of a patient suffering from Fanconi syndrome. The authors have merely used the urine of the patients as a source of large amounts of CFD because it is known that they are affected by proteinuria and for this reason excrete particularly high amounts of protein via the urine. However, the authors have not realized the diagnostic relevance of the identified isoform of CFD.

According to the invention an "isoform of the complement factor D" or "isoCFD" refers to a derivative of CFD which differs from the mature or active form of CFD, in the following referred to as "CFD", and from the immature form of CFD (proCFD). According to a preferred embodiment isoCFD has an isoelectric point (pI) other than CFD and proCFD. According to a further preferred embodiment isoCFD has a molecular weight other than CFD and proCFD. According to a still further preferred embodiment isoCFD comprises in its amino acid sequence in at least one position an amino acid other than CFD and proCFD. According to a still further embodiment the isoCFD according to the invention is extended in contrast to CFD by at least one amino acid, and/or shortened in contrast to proCFD by at least one amino acid, at the C terminus and/or preferably at the N terminus.

According to the invention isoforms of CFD (isoCFD) do, however, not refer to mutated forms of CFD, as for example the point mutated CFD forms described by Sprong et al. (l.c). According to the invention isoCFD does also not refer to forms of CFD which comprise polymorphisms such as single nucleotide polymorphisms (SNPs) as described in the US 2003/0092620.

The amino acid sequence of the mature or active form of the human CFD is shown in the attached sequence listing under SEQ ID No. 1. The immature form of human CFD (proCFD) is shown in the attached sequence listing under SEQ ID No. 2.

Mature human CFD comprises a theoretical isoelectric point of 6.85 and immature CFD (proCFD) of 7.99. The isoforms of CFD (isoCFD) identified by the inventors comprise theoretical isoelectric points of <7.99 and >6.85. The theoretical isoelectric points can be calculated by the method which is described in Bjellqvist (1993), The focusing positions of polypeptides in immobilized pH gradients can be predicted from the amino acid sequences, electrophoresis, Vol. 14(10), pages 1023 to 1031.

Because of these differences an "isoCFD" can be simply and reliably distinguished from CFD and proCFD by means of established molecular biological methods, such as the isoelectric focusing, a separation according to the molecular weight or the mass, for example by means of SDS gel electrophoresis or mass spectrometry.

"At least one isoCFD" according to the invention means that the biological sample can also contain at least two, at least three, at least four or more different isoCFD. The examination in step (2) can be directed not only to the presence of one isoCFD but also on several different isoCFD or a pattern of different isoCFD.

According to the invention "living being" is to be understood to include any living being, whereas the method according to the invention is preferably to be used in a mammal and further preferably in a human being.

According to the invention a "biological sample" is to be understood as referring to any sample potentially containing CFD, such as a blood, urine, synovial fluid or sputum sample but also another tissue sample, for example from the fatty tissue.

The inventors have realized for the first time that isoCFD can be used as a diagnostic marker for a disease or a risk for the development of a disease. For this reason isoCFD can also be used as a marker in diagnostics during therapy ("companion diagnostics").

"Making a diagnosis" includes the determination that there is a disease or a risk for a disease or disorder (positive diagnosis) or there is not (negative diagnosis). It also includes a stratification of the living being, what means the allocation of a degree of severity of the disease or a degree of risk for a disease or the progression of the disease.

Against this background the invention also is an isoform of the complement factor D (isoCFD) as a diagnostic marker for a disease or a risk for the development of a disease.

This embodiment of the invention also relates to a pattern of isoCFD which is detectable in a biological sample of a living being, as a diagnostic marker for a disease or a risk for the development of a disease.

According to the invention, in this context a "pattern" of isoCFD refers to a composition of different isoforms of CFD or a set of isoCFD which is characteristic for the living being. These different isoforms can for example be separated in one- or two-dimensional gel electrophoresis or by means of mass spectrometry. Via these methods different measurement signals can be assigned to different isoCFD. A characteristic signal pattern is obtained. If this pattern differs from a pattern of a healthy reference living being a positive diagnosis can be made.

The features, characteristics of the diagnostic method according to the invention along with its preferred embodiments apply to the isoform of the complement factor D according to the invention in a similar manner.

The problem underlying the invention is herewith completely solved.

In an embodiment the method according to the invention is a method for the diagnosis of a disease which is mediated via the alternative pathway of the complement system, or a risk for the development of such a disease. According to an alternative preferred further development of the method according to the invention the disease is such a disease which is mediated via the complement factor D.

This measure has the advantage that for the first time a reliable and highly sensitive method is provided by means of which the patients can be stratified with respect to their risk to be affected by a disease which is mediated via the alternative pathway of the complement system or the complement factor D. Such diseases are sufficiently described in the prior art, for example in the publication of Holers (2008; l.c.) or in the database "MalaCards" of the Weizmann Institute of Science. They preferably include diseases which are selected from the group consisting of obesity, Simpson-Golabi-Behmel syndrome (SGBS), cerebral autosomal dominant arteriopathy with subcortical infarcts and leukoencephalopathy (CARASIL), diabetes mellitus type 2, factor D deficiency, atypical haemolytic uraemic syndrome (aHUS), paroxysmal nocturnal hemoglobinuria (PNH), age related macula degeneration (AMD), rheumatoid arthritis (RA), systemic lupus erythematosus (SLE), IgA nephropathy, Henoch-Schönlein purpura, idiopathic membranoproliferative glomerulonephritis, post streptococcal disease, myocarditis, multiple sclerosis (MS), traumatic brain injury, traumatic spinal cord injury, intestinal and renal reperfusion injury, anti-phospholipid syndrome (APS), habitual abort syndrome, pre-eclampsia, asthma, ANCA associated pauci immune retinal vasculitis, antibody mediated skin disease, meningococcal infection, anorexia nervosa, rhinitis, Hodgkin's lymphoma, non-Hodgkin's lymphoma, neuronitis, liposarcoma, sepsis, uremia, endotheliitis, coronary heart disease, multiple myeloma, Hiv 1, intracranial aneurysm, rheumatoid arthritis, McCune Albright syndrome, peritonitis, hepatitis, cerebritis, aortic aneurysm, Fleck corneal dystrophy, heart attack, dilated cardiomyopathy, fibrous dysplasia, LAMM syndrome ("deafness with labyrithine aplasia microtia and microdontia"), intracranial embolism.

In an embodiment of the method according to the invention in step (2) the biological sample is examined for the presence of at least such an isoCFD which, in comparison with CFD, is extended at its N terminus by 1 to 4, i.e. by 1 (isoform "−4") or by 2 (isoform "−3") or by 3 (isoform "−2") or by 4 amino acids (isoform "−1").

In another embodiment in step (2) the biological sample is examined for the presence of at least such an isoCFD which, in comparison with proCFD, is shortened at its N terminus by 1 to 4, i.e. by 1 (isoform "−1") or by 2 (isoform "−2") or by 3 (isoform "3") or by 4 amino acids (isoform "−4").

As the inventors were able to find out such isoforms of CFD can be found in a biological sample or body fluids of individuals, such as blood or urine, which either are affected by any of the mentioned diseases or which have a risk for a disease.

In an embodiment in step (2) the biological sample is examined for the presence of an isoCFD which, in comparison to the CFD, is extended at its N terminus by an amino acid sequence which is selected from the group consisting of: arginine (R), glycine-arginine (GR), arginine-glycine-arginine (RGR) and proline-arginine-glycine-arginine (PRGR), and/or which, in comparison to proCFD, is shortened at its N terminus by an amino acid sequence which is selected from the group consisting of: proline (P), proline-proline (PP), proline-proline-arginine (PPR), and proline-proline-arginine-glycine (PPRG).

This measure has the advantage that it is specifically searched for such isoforms which, according to the findings of the inventors, are appropriate indicators or biomarkers.

In another embodiment of the method according to the invention the isoCFD comprises an amino acid sequence which is selected from the group consisting of: SEQ ID No. 3, SEQ ID No. 4, SEQ ID No. 5, SEQ ID No. 6, and SEQ ID No. 7.

This measure has the advantage that by the provision of the amino acid sequence of the respective isoforms of CFD a still more reliable identification of the biomarkers is possible.

In another embodiment of the method according to the invention the biological sample is selected from the group consisting of: biological liquid, in particular blood serum and urine, or fatty tissue.

This measure has the advantage that such a starting material is provided for the carrying out the method according to the invention, within which the isoforms of CFD can be detected in a particularly well manner.

In another embodiment of the method according to the invention in step (3) a positive diagnosis is made if the concentration of isoCFD in the biological liquid is ≥0.01 µg/ml, preferably ≥0.1 µg/ml, further preferably ≥1 µg/ml, further preferably ≥10 µg/ml, and further preferably ≥100 µg/ml. A negative diagnosis is made if the concentration of isoCFD in the biological sample is ≤0.01 µg/ml, preferably ≤0.1 µg/ml, further preferably ≤1 µg/ml, further preferably ≤10 µg/ml, and further preferably ≤100 µg/ml.

This measure has the advantage that on the basis of thresholds an even more precise diagnosis is possible. The indicated concentrations refer to an individual isoform of CFD. According to an alternative configuration the concentrations given refer to the population of all isoforms of CFD.

In another embodiment of the method according to the invention in step (2) the examination of the biological sample is carried out by means of mass spectrometry and/or one-dimensional gel electrophoresis and/or two-dimensional gel electrophoresis (2-DE), whereas further preferably in the one-dimensional gel electrophoresis an isoelectric focusing (IEF) of the sample is carried out, and/or in one dimension of the 2-DE an isoelectric focusing (IEF) of the sample is carried out, and/or in one or the further dimension a separation of the sample according to the molecular weight is carried out.

This measure has the advantage that molecular biological methods are employed which allow the detection of isoCFD in a particular simple manner and reliable manner.

The one-dimensional gel electrophoresis besides the IEF has the advantage over the 2-DE that it is less prone to errors, more reproducible and faster to carry out. The time needed for analysis is reduced from 3 days to less than 24 hours and provides the opportunity to analyze 40 samples/gel in parallel in a reproducible manner.

In contrast, the mass spectrometric analysis has the advantage that it does not require any use of antibodies.

In another embodiment of the method according to the invention following the one-dimensional gel electrophoresis and/or the two-dimensional gel electrophoresis a Western-blot analysis of the biological sample is carried out.

In the context of this measure the isoCFD which were transferred onto a carrier membrane can be detected by means of specific antibodies in a reliable and highly sensitive manner. This analytical method is especially well suited for the method according to the invention.

Another subject matter of the present invention is a nucleic acid molecule which encodes an isoform of complement factor D (isoCFD).

Such a nucleic acid molecule when used in an appropriate expression system allows the production of an isoCFD. The nucleic acid molecule can be DNA, RNA, cDNA etc. Also included are vectors and plasmids which contain the respective coding sequences. The nucleic acid molecule according to the invention can preferably encode an isoCFD comprising an amino acid sequence which is selected from the group consisting of: SEQ ID No. 3, SEQ ID No. 4, SEQ ID No. 5, SEQ ID No. 6, and SEQ ID No. 7.

Another subject matter of the invention is a method for identifying active agents, comprising the following steps:
(1) Providing a biological sample which contains isoCFD in a concentration [$C_{pre}$] and/or activity [$A_{pre}$],
(2) Incubation of the biological sample with a test substance under physiological conditions,
(3) Measuring the concentration of isoCFD [$C_{post}$] and/or the activity of isoCFD [$A_{post}$],
(4) Identifying the test substance
 as an active substance if [$C_{post}$]≠[$C_{pre}$] and/or [$A_{post}$]≠[$A_{pre}$], or
 as a non-active substance, if [$C_{post}$]=[$C_{pre}$] and [$A_{post}$]=[$A_{pre}$].

By means of such a screening method for the first time active agents can be found in a very direct manner, which allow the treatment or prevention of diseases which are mediated via the alternative pathway of the complement system or the complement factor D, respectively. A test substance qualifies as an active substance if, e.g., because of the incubation of the biological sample with the test substance the concentration of isoCFD and/or its activity is changed, preferably lowered. In this context [$C_{pre}$] and/or [$A_{pre}$] are known.

The method according to the invention is for this reason also applicable as a high throughput method, for example for the screening of libraries of substances.

According to the invention "physiological conditions" refer to such conditions which prevail in the organism, for example a temperature of 37° C. and a pH value of 7. Such conditions reflect the effect of the test substance and the interaction of the components of the complement system, in particular of the alternative pathway, in the body of an individual to be treated.

According to the invention "activity of isoCFD" means the enzymatic or catalytic activity of the isoform of CFD in the biological sample or the organism belonging thereto, which can be measured by test systems known to the skilled artisan.

According to the invention "concentration of isoCFD" refers to the amount of isoCFD in the biological sample or the organism belonging thereto per volume unit.

Another subject matter of the present invention is a method for the identification of an active substance, comprising the following steps:
(1) Providing a biological sample,
(2) Determination of the isoforms of the complement factor D (isoCFD) contained in the biological sample to obtain a first pattern $P_{pre}$,
(2) Incubation of the biological sample with a test substance under physiological conditions,
(3) Determination of the isoCFD contained in the biological sample to obtain a second pattern $P_{post}$,
(4) Identifying the test substance
 as an active substance if $P_{post}$≠$P_{pre}$, or
 as a non-active substance if $P_{post}$=$P_{pre}$.

This variant of the screening method according to the invention uses a so-called pattern matching to find active substances.

According to the invention a "pattern" of isoCFD means a composition of different isoforms of CFD or a set of isoCFD which are characteristic for the sample. These different isoforms can be separated from each other e.g. by means of a two-dimensional gel electrophoresis or by means of a mass spectrometry. With these methods the different isoCFD can be allocated to different measurement signals. A characteristic signal pattern is obtained. If then the first pattern $P_{pre}$ obtained before the incubation of the biological sample differs from the pattern $P_{post}$ obtained after the incubation of the biological sample an identification of the test substance as an active substance is made. If the test substance has no effect on the pattern the test substance is excluded from the active substances.

The features, characteristics and preferred embodiments of the diagnostic method according to the invention also apply for both of the screening methods according to the invention and vice versa.

It is to be understood that the afore-mentioned features and those to be explained in the following cannot only be used in the combination indicated in each case but also in other combinations or in isolated position without departing from the scope of the present invention.

The present invention is now explained in more detail by means of embodiments, which result in further features, characteristics and advantages of the invention. The embodiments are of a purely illustrative character and do not restrict the scope of the present invention.

DESCRIPTION OF PREFERRED EMBODIMENTS

1. Material and Methods

Patient Samples

Serum samples from five morbidly obese patients were received from Professor Matthias Blither, University Hospital Leipzig, Germany. Fasting blood samples were collected, and the serum was separated by centrifugation at 3000×g, for 10 minutes an stored at −80° C. for the further analysis.

Serum samples from a healthy test person was withdrawn in the Department for Ophthalmology at the University of Tübingen, separated by centrifugation at 3000×g for 10 minutes and stored at −80° C. until the further analysis. Samples from retinal pigment epithel (RPE) were received from the Eye Clinic of the University of Tübingen, visceral and subcutaneous fat were obtained from the surgical clinic. The tissue samples were homogenized and stored at −80° C. until the further analysis.

Zell Lines

The human monocytic cell line U937 cells (ATTC; Manassas, Va.) were cultivated in RPMI1640 medium supplemented with 10% FBS and 100 U/ml penicillin and 100 µg/ml streptomycin at 37° C. in an incubator with 5% $CO_2$ until a cell density of $1×10^6$ cells/ml was reached. The cells were then washed with PPS and further incubated for 72 hours in serum free medium. Conditioned medium was collected and concentrated by using 3 kDa cutoff spin concentrators.

The human preadipocyte cell line from a patient with Simpson-Golabi-Behmel syndrome (SGBS) was received from Professor Martin Babitsch, University of Ulm, Germany. The cells were differentiated into adipocytes within 14 days and cultivated in serum free medium like the U937 cells.

Treated Recombinant proCFD

Recombinant human proCFD which was recombinantly produced in HEK293 cells (non-purified cell culture supernatants) was cultivated after the addition of various recombinant proteases (MASP1, MASP3, C1R, and C1S) at 37° C. over night.

One-Dimensional Gel Electrophoresis/Isoelectric Focusing

Precast gels of the type IEFGel 6-111 40S (EDC, Tübingen) were positioned in a multiphor II chamber (GE Healthcare) in a way that the pockets of the gel project towards the anode. 10 µL of the sample were each pipetted free of air bubbles into the gel pockets. The isoelectric focusing (IEF) was performed as follows: 500 V for 20 minutes, 1500 V for 90 minutes, 1900 V for 20 minutes.

Two-Dimensional Gel Electrophoresis (2-DE)/Isoelectric Focusing

Immobiline DryStrips, with a linear pH gradient of 3 to 10, 18 cm (GE Healthcare) were hydrated for 20 hours using a buffer containing 8 M urea, 2% CHAPS, 65 mM DTT % (v/v), 1% Pharmalyte IPG buffer 3-10, and bromophenol blue (Trace). 200 µg of serum proteins were loaded by in-gel rehydration. For the cell culture supernatants 1 ml serum free medium was precipitated, resuspended in rehydration buffer and loaded in the same way.

The isoelectric focusing (IEF) was performed as follows: 500 V for 1 hour, 1000 V for 1 hour, 8000 V for 3 hours, and finally 10,000 V for 4 hours. The focused IPG strips were equilibrated for 15 minutes in 4 ml equilibration solution containing 6 M urea, 75 mM Tris-HCl buffer pH 6.8, 2% (w/v) SDS, 29.3% (v/v), 30% glycerol containing 65 mM DTT. The DTT was replaced with 260 mM iodoacetamide in the equilibration solution and an equilibration for additional 15 minutes was carried out.

A piece of approximately 7 cm containing all CFD isoforms was cut out from the 18 cm IPG strip and subjected to a second dimension electrophoresis using 10 cm 10% SDS-PAGE gels (Bio-Rad).

Detection of CFD, proCFD, and isoCFD

For the transfer of the proteins onto a blotting membrane the contact blot method is used. At first, the PVDF membrane is activated in 100% methanol and then rinsed three times for 10 min in 1×TBS buffer. After the isoelectric focusing the gel was briefly cleaned and placed on a glass plate with the support downward. The blotting membrane was then directly laid onto the gel and any air bubbles were rolled out. Five dry Whatman filter papers, a second glass plate and 1-2 kg weight were stacked on top, and after 45 min the membrane could be used for the subsequent immunological detection. The separated CFD isoforms were detected by using a goat antibody against human CFD as primary antibody (AF1824; R & D Systems, dilution 1:500).

Mass Spectrometry

The examinations by mass spectrometry were carried out by using standard protocols in the mass spectrometer QExactive Orbitrap.

2. Results

Figure 1:
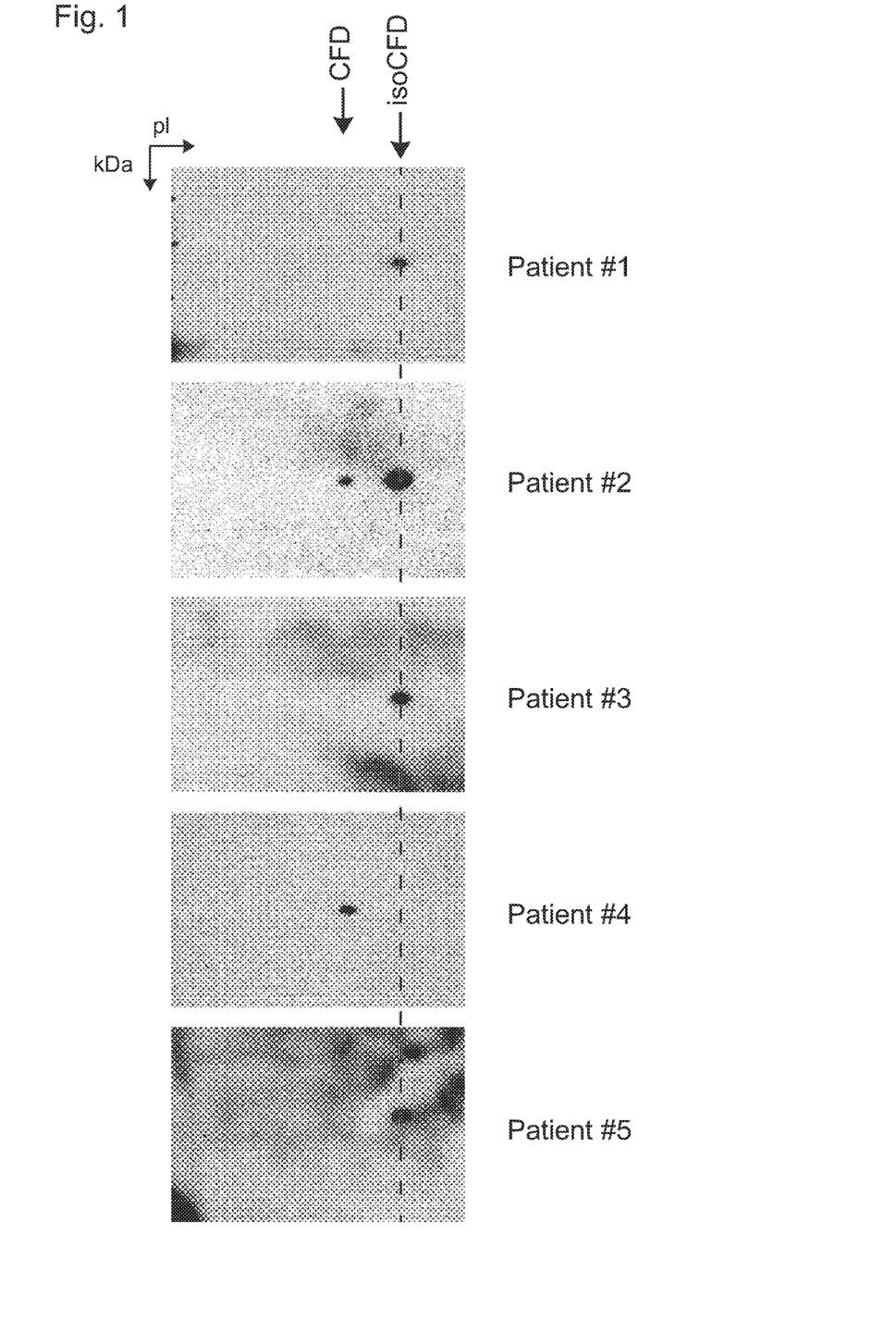
FIG. 1 specific detection of CFD isoforms in the serum of five different obesity patients by using a two-dimensional Westernblot analysis.

In the FIG. 1 the result of a two-dimensional gel electrophoretically separation and Westernblot analysis of blood sera from five patients with morbid obesity is shown. In the patients 1, 2, 3, and 5 isoforms, (isoCFD) of CFD can be found (dashed line). On the left, in the patients 2 and 4 the mature or active form of CFD (CFD) can be found. The isoforms of CFD are, according to the findings of the inventors, possibly incompletely processed variants of proCFD.

Figure 2:
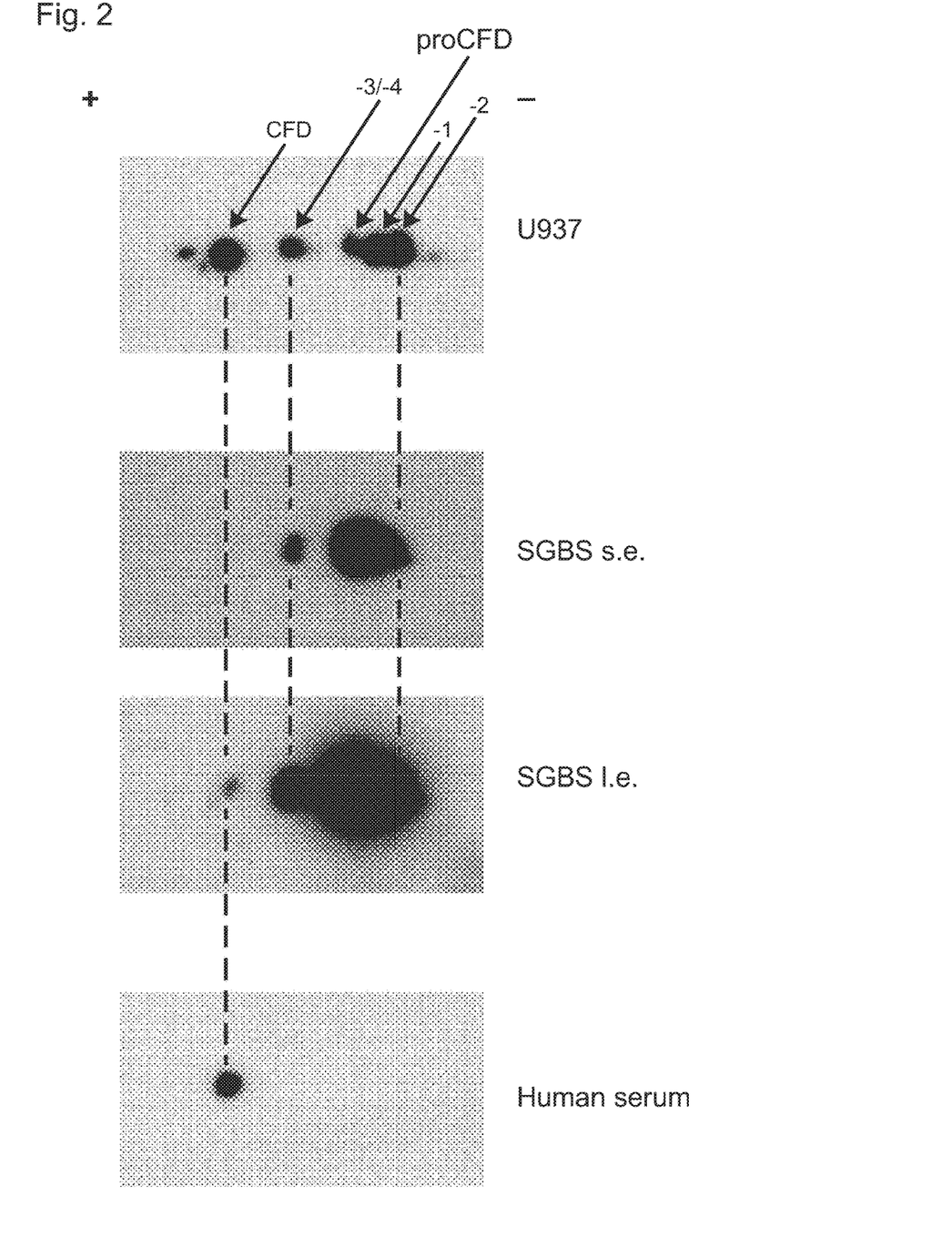
FIG. 2 specific detection of CFD isoforms in a human monocyte cell line (U937) and a fat cell line from patients with Simpson-Golabi-Behmel syndrome (SGBS) in comparison with human serum of a healthy reference person.

In the FIG. 2 the result is shown of a gel electrophoretically two-dimensional separation and an analysis by means of a Westernblot of supernatants from human monocytes (U937) and adipocytes from a patient with Simpson-Golabi-Behmel syndrome (SGBS) in comparison to human serum from a healthy reference person is shown. Both of the illustrations concerning SGBS differ in the duration of the exposition of the X-ray film. In the first case a short exposure (s.e.) and in another case a long exposure (l.e.) for a better visualization were carried out. All of the illustrations show each a typical pattern of isoCFD which differs depending on the examined sample. There it can be shown that only one form of CFD is detectable in the blood serum of the healthy donor. It comprises an isoelectric point of a bit less than 7.0. In the U937 and SGBS cells isoforms of CFD can be detected which are referred to as "−4", "−3", "−2", and "−1".

In another experiment blood serum from patients with cerebral autosomal recessive arteriopathy with subcortical infarcts and leukoencephalopathy (CARASIL) was separated by gel electrophoresis over two dimensions. In the following Westernblot analysis again several isoforms of CFD could be detected, which were not detectable in a healthy reference person (data not shown).

Figure 3:
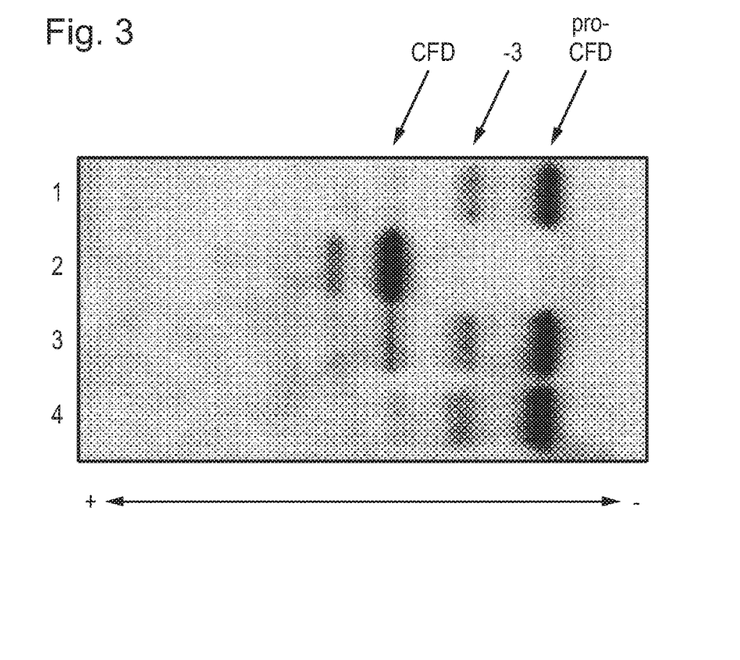
FIG. 3 Actual determination of CFD isoforms. Isoelectric focusing of 4 CFD containing samples in a one-dimensional gel electrophoresis, which were treated with different proteases. One of these proteases is capable of completely converting proCFD into the active enzyme (CFD) (lane 2), whereas another causes a partial activation (lane 3). In all lanes further isoforms are detectable.

In the FIG. 3 the result of a one-dimensional gel electrophoresis with isoelectric focusing and Westernblot analysis of proCFD which was treated with different proteases, is shown. Different prominent forms can be found (arrows), inter alia the isoCFD "−3". ProCFD treated with MASP1 was not strongly processed (lane 1), whereas proCFD treated with MASP3 was almost completely converted into active CFD and even shows further processed forms (lane 2). The treatment with C1R resulted in a partial processing/activation (lane 3), whereas the convertase C1S hardly shows effects (lane 4, like MASP1). After a treatment with C1R and C1S the isoCFD "−3" can also be found.

Figure 4:
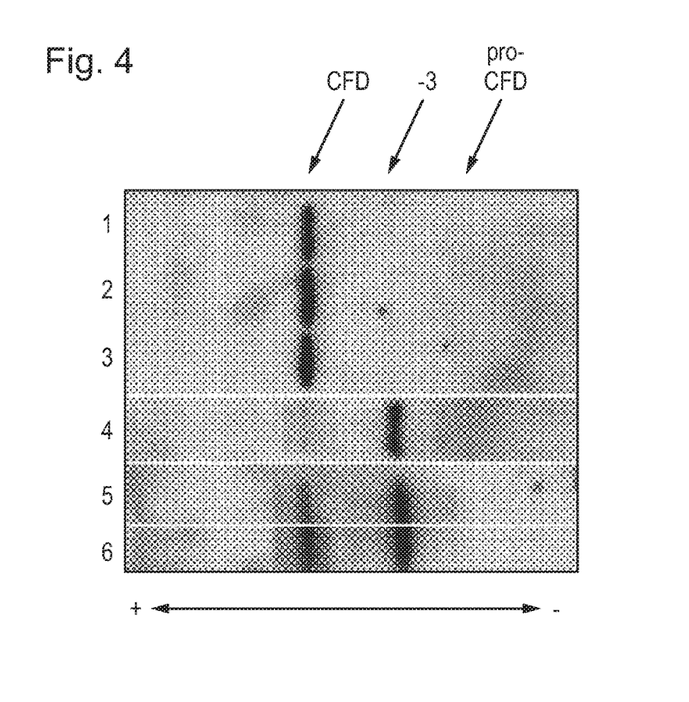
FIG. 4 Determination of CFD isoforms in clinical material. IEF immunoblot after a one-dimensional gel electrophoresis of 1-3) serum, 4) retinal pigment ephitel, 5) visceral fat, and 6) subcutaneous fat. In contrast to serum (lanes 1-3) in healthy pigment epithel almost no processing into active CFD takes place (lane 4), whereas in the samples of fatty tissue a partial activation takes place (lanes 5-6).

In the FIG. 4 the result of an isoelectric focusing after a one-dimensional gel electrophoresis and a Westernblot analysis of a blood serum and several tissue lysates is shown, namely such from retinal pigment epithel (RPE) and visceral and subcutaneous fat. In the blood serum (lanes 1-3, replicates) exclusively processed mature CFD is detectable (arrow with "CFD"). Both in the extracts of RPE (lane 4) but also in the two fat tissue samples (lanes 5 and 6) the partially processed isoCFD "−3" (arrow with "−3") is the most prominent one while more isoforms can be detected. It is to be noted that the completely non-processed form of the inactive proenzyme ("proCFD") is hardly detectable.

To establish a completely different detection method which is independent from a detection with antibodies a targeted analysis by mass spectrometry for the processed N terminus of profactor D was developed. After a method was set up on the QExactive Orbitrap mass spectrometer by the aid of synthetic peptides which cover parts of the "core" of CFD but also the two main forms of the N terminus, recombinant proCFD was overexpressed in HEK cells and detected in the supernatant by means of a limited proteolysis and a subsequent peptide separation and detection. These supernatants were additionally preincubated with different proteases to cause a possible conversion of proCFD.

Figure 5:
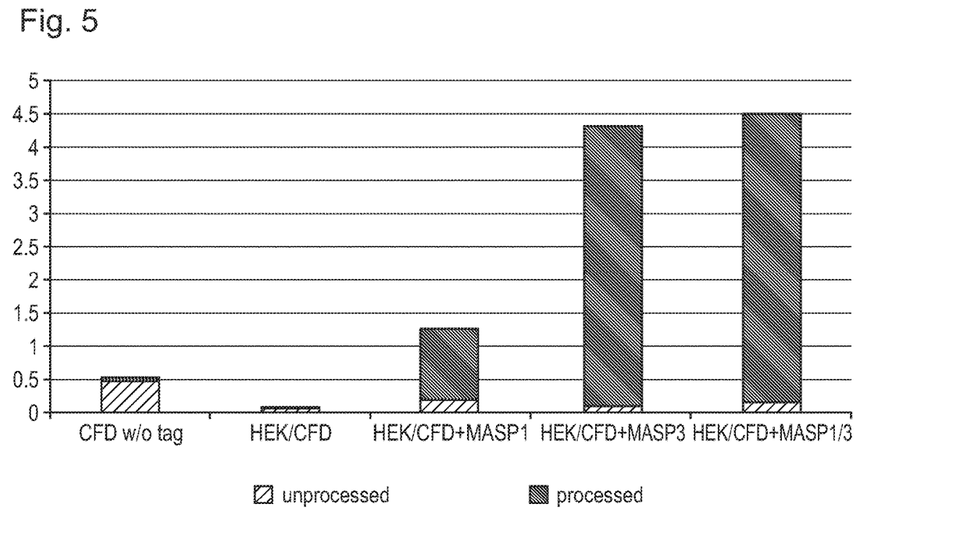
FIG. 5 Determination of the processed N terminus of profactor D by means of targeted mass spectrometry (sum of the y7 ions ILGGREAE). Cell culture supernatants (HEK/CFD) containing proCFD were incubated with different recombinant proteases, prepared for the protein analysis by mass spectrometry, and finally targeted peptides were measured in the QUxactice Orbitrap i) for the core protein (2 peptides), ii) for the processed N terminus, and iii) for the non-processed N terminus. After the normalization for the intensities of the signals of the peptides from the core protein the degree of the processing was relatively quantified. Only in the presence of the protease MASP3 a successful activation of proCFD could be shown in this test system.

The results of the examination by mass spectrometry are shown in FIG. 5: proCFD containing cell culture supernatants (HEK/CFD) were incubated with different recombinant proteases, prepared for the protein analysis by mass spectrometry, and finally peptides i) for the core protein (2 peptides), ii) for the processed N terminus, and iii) for the non-processed N terminus were measured in the QExactive Orbitrap in an targeted manner. After the normalization for the signal intensities of the peptides from the core protein the degree of the processing was relatively quantified. Only the proteases from the MASP family, i.e. L. MASP3 show a successful activation of proCFD.

The described experiment is de facto a convertase activity test which is thought as having great potential in the development and diagnostics.

According to the findings of the inventors, specific amino acid sequences can be assigned to the found isoforms, as shown in the following table form:

TAB. 1

| CFD variant or isoform | N terminal sequence | Theoretical pI | Complete sequence |
|---|---|---|---|
| proCFD | *PPRGRILGGR* SEQ ID No. 7 | 7.99 | SEQ ID No. 2 |
| −1 | *PRGRILGGR* SEQ No. 8 | 7.99 | SEQ ID No. 3 |
| −2 | *RGRILGGR* SEQ ID No. 9 | 7.78 | SEQ ID No. 4 |
| −3 | *GRILGG* SEQ ID No. 10 | 7.26 | SEQ ID No. 5 |
| −4 | *RILGGR* SEQ ID No. 11 | 7.26 | SEQ ID No. 6 |
| mature | ILGGR SEQ ID No. 12 | 6.85 | SEQ ID No. 1 |

Identified CFD variants or CFD isoforms in U937 and SGBS cells;
proCFD = immature form of CFD;
mature = mature form of CFD (CFD);
"−1", "−2", "−3", "−4" = isoforms of CFD;
the amino acids shown in italics can be found in the proCFD, the amino acids not shown in italics limit the mature CFD.

In the following the N terminus of CFD or proCFD and the corresponding isoforms are shown. The amino acids of the mature protein are shown in large letters in normal font, the section which can be found in the isoforms of CFD and proCFD is shown in italics, and the section relating to the signal peptide is underlined:

(SEQ ID No. 13)
<u>MHSWERLAVLVLLGAAACAA</u>*PPRGRILGGR*

According to the findings of the inventors the identified isoforms of CFD differ from the proCFD (SEQ ID No. 2) by an N terminal shortening of the peptide by one amino acid (proline, "−1"; SEQ ID No. 3), two amino acids (proline-proline, "−2"; SEQ ID No. 4), three amino acids (proline-proline-arginine, "−3"; SEQ ID No. 5) or four amino acids (proline-proline-arginine-glycine, "−4"; SEQ ID No. 6) or from the mature CFD (SEQ ID No. 1) by correspondingly added amino acids. The inventors assume that the isoforms are based on an incomplete processing of proCFD.

The inventors could show that the detection of isoCFD can be made not only via conventional gel electrical methods with isoelectric focusing but also via modern mass spectrometrical tests. This also allows the detection of the conversion of proCFD in biological samples.

3. Conclusion

The inventors have realized for the first time that isoforms of CFD are appropriate diagnostic or biological markers. On the basis of a biological sample of a living being, such as a blood or urine sample, depending on the presence or the absence of these markers a statement about a disease or a precondition for a disease can be made, in particular about a disease which is mediated via the alternative pathway of the complement system. Furthermore the isoforms of CFD can be used to identify new active substances by means of which diseases can be treated or prevented which are mediated via the alternative pathway of the complement system, in particular via the complement factor D.

SEQUENCES

SEQ ID No. 1: amino acid sequence of mature human CFD (CFD)
SEQ ID No. 2: immature human CFD (proCFD)
SEQ ID No. 3: isoform of human CFD (isoCFD "−1")
SEQ ID No. 4: isoform of human CFD (isoCFD "−2")
SEQ ID No. 5: isoform of human CFD (isoCFD "−3")
SEQ ID No. 6: isoform of human CFD (isoCFD "−4")
SEQ ID No. 7: N terminus of proCFD
SEQ ID No. 8: N terminus of isoCFD "−1"
SEQ ID No. 9: N terminus of isoCFD "−2"
SEQ ID No. 10: N terminus of isoCFD "−3"
SEQ ID No. 11: N terminus of isoCFD "−4"
SEQ ID No. 12: N terminus of CFD
SEQ ID No. 13: N terminus of CFD/proCFD/signal peptide

What is claimed is:

1. A method for detecting an isoform of complement factor D (isoCFD) in a living being, comprising the following steps:
   (1) providing a biological sample of the living being, and
   (2) measuring the biological sample for the presence of at least one isoCFD, which consists of an amino acid sequence selected from the group consisting of: SEQ ID No. 3, SEQ ID No. 4, SEQ ID No. 5, and SEQ ID No. 6.

2. The method of claim 1, wherein the biological sample is selected from the group consisting of: blood serum, urine; joint fluid, sputum, and fatty tissue.

3. The method of claim 1, wherein in step (2) the measuring of the biological sample is carried out by: mass spectrometry, one-dimensional gel electrophoresis or two-dimensional gel electrophoresis (2-DE).

4. The method of claim 3, wherein in the one-dimensional gel electrophoresis an isoelectric focusing of the sample is carried out.

5. The method of claim 3, wherein in the 2-DE in one dimension an isoelectric focusing of the sample is carried out and in another dimension a separation of the sample according to the molecular weight is carried out.

6. The method of claim 4, wherein after the one-dimensional gel electrophoresis a Western blot analysis of the biological sample is carried out.

7. The method of claim 5, wherein after the 2-DE a Western blot analysis of the biological sample is carried out.

* * * * *